United States Patent [19]
Ushikubo et al.

[11] Patent Number: 5,422,328
[45] Date of Patent: Jun. 6, 1995

[54] PROCESS FOR PREPARING A CATALYST USEFUL FOR PRODUCING A NITRILE

[75] Inventors: Takashi Ushikubo; Itaru Sawaki, both of Yokohama; Kazunori Oshima, Machida; Kei Inumaru, Tokyo; Satoshi Kobayakawa, Yokkaichi; Ken-ichi Kiyono, Machida, all of Japan

[73] Assignee: Mitsubishi Kasei Corporation, Tokyo, Japan

[21] Appl. No.: 172,819

[22] Filed: Dec. 27, 1993

[30] Foreign Application Priority Data

Dec. 24, 1992 [JP] Japan ................................ 4-344717
Feb. 5, 1993 [JP] Japan ................................ 5-018917

[51] Int. Cl.⁶ .......................... B01J 23/22; B01J 23/28
[52] U.S. Cl. ............................ 502/312; 502/309; 502/311; 502/313; 502/321; 502/322; 502/353; 502/354; 558/319

[58] Field of Search ............... 502/305, 312, 321, 311, 502/309, 313, 322, 353, 354; 558/319

[56] References Cited

U.S. PATENT DOCUMENTS

| | | | |
|---|---|---|---|
| 4,797,381 | 1/1989 | Bartek et al. | 502/312 |
| 4,966,990 | 10/1990 | Otake et al. | |
| 5,049,692 | 9/1991 | Hatano et al. | |
| 5,206,201 | 4/1993 | Kishimoto et al. | 502/206 |
| 5,231,214 | 7/1993 | Ushikubo et al. | |
| 5,281,745 | 1/1994 | Ushikubo et al. | |

*Primary Examiner*—Anthony McFarlane
*Attorney, Agent, or Firm*—Oblon, Spivak, McClelland, Maier & Neustadt

[57] ABSTRACT

A process for preparing a catalyst useful for producing a nitrile by a gas phase catalytic oxidation reaction of an alkane with ammonia, which comprises drying a solution or slurry containing molybdenum, vanadium and tellurium by a spray drying method or a freeze-drying method and heat-treating the resulting dried product.

30 Claims, 1 Drawing Sheet

PROCESS FOR PREPARING A CATALYST USEFUL FOR PRODUCING A NITRILE

The present invention relates to a process for preparing a catalyst useful for producing a nitrile. Particularly, it relates to a process for producing a catalyst useful for producing a nitrile using an alkane as starting material.

Nitriles such as acrylonitrile and methacrylonitrile have been industrially produced as important intermediates for the preparation of fibers, synthetic resins, synthetic rubbers and the like. The most popular method for producing such nitriles is to subject an olefin such as propylene or isobutene to a catalytic reaction with ammonia and oxygen in the presence of a catalyst in a gas phase at a high temperature.

On the other hand, in view of the price difference between propane and propylene or between isobutane and isobutene, an attention has been drawn to developing a method for producing acrylonitrile or methacrylonitrile by a so-called ammoxidation reaction method wherein a lower alkane such as propane or isobutane is used as starting material, and it is catalytically reacted with ammonia and oxygen in a gas phase in the presence of a catalyst.

For example, there have been reports on a Mo—Bi—P—O catalyst (Japanese Unexamined Patent Publication No. 16887/1973), a V—Sb—O catalyst (Japanese Unexamined Patent Publication No. 33783/1972, Japanese Examined Patent publication No. 23016/1975 and Japanese Unexamined Patent Publication No. 268668/1989), a Sb—U—V—Ni—O catalyst (Japanese Examined Patent Publication No. 14371/1972, a Sb—Sn—O catalyst (Japanese Examined Patent Publication No. 28940/1975), and a V—Sb—W—P—O catalyst (Japanese Unexamined Patent Publication No. 95439/1990).

However, none of these methods is fully satisfactory in the yield of the intended nitriles. Further, such methods usually require a very high reaction temperature at a level of about 500° or higher, and therefore, they are not advantageous from the viewpoint of the material for the reactors, the production costs, etc. In order to improve the yield of nitriles, it has been proposed to add a small amount of an organic halide, an inorganic halide or a sulfur compound, or to add water to the reaction system. However, the former three methods have a problem of possible corrosion of the reaction apparatus, while the latter water-adding method has a problem of formation of by-products by side reactions or a problem of their treatment. Thus, each method has a practical problem for industrial application.

On the other hand, the present applicants have reported on a Mo—V—Te—Nb—O catalyst (Japanese Unexamined Patent Publication No. 257/1990). With this catalyst, the optimum reaction temperature is relatively low at a level of from 400° to 450° C., and an improvement in the yield of a nitrile is observed. Further, Japanese Unexamined Patent Publication No. 257/1990 discloses a process for producing the catalyst, wherein an aqueous solution of catalyst components is heated and concentrated and then evaporated to dryness at 130° C., and the dried product is calcined at a temperature of from 350° to 650° C. to obtain the catalyst. Further, the same publication presents a general explanation that the catalyst can be molded and adjusted to a proper particle size and shape depending upon the scale, system, etc. of the reaction.

It is an object of the present invention to improve the process for producing a nitrile using an alkane as starting material, particularly to improve the process for preparing the catalyst useful for such production, so that the nitrile can be produced more efficiently.

The present inventors have further continued the study on the process for producing a nitrile using an alkane as starting material primarily with an aim to improve the above Mo—V—Te—Nb—O catalyst and as a result, have found a Mo—V—Te—X—O catalyst wherein X is one or a plurality of specific elements, and X may include Nb (Japanese Patent Application No. 104382/1991). Further, they have found it possible to improve the yield of a nitrile remarkably by using a certain specific crystal structure among the same Mo—V—Te—X—O catalysts (Japanese Patent Application No. 199573/1991).

The present inventors have exerted an effort for a further study on the basis of the above-mentioned recent research results and have found it possible to obtain a catalyst which is further improved over the above conventional catalysts by employing a certain specific means for the process for preparing a catalyst containing molybdenum, vanadium and tellurium. The present invention has been accomplished on the basis of this discovery.

Thus, the present invention provides a process for preparing a catalyst useful for producing a nitrile by a gas phase catalytic oxidation reaction of an alkane with ammonia, which comprises drying a solution or slurry containing molybdenum, vanadium and tellurium by a spray drying method or a freeze-drying method and heat-treating the resulting dried product.

Figure 1:
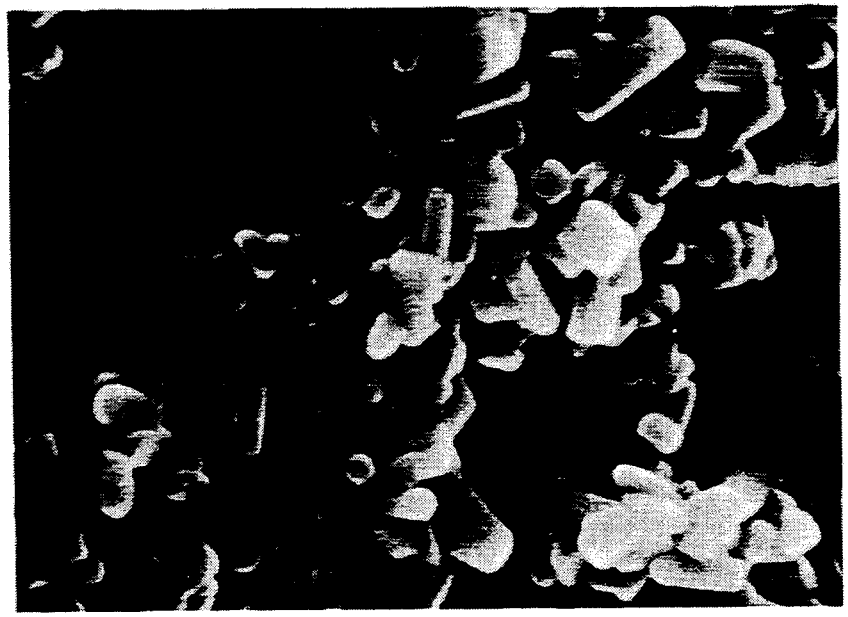
FIG. 1 is a photograph showing the surface of the catalyst particles obtained in Example 14 (50,000 magnifications).

Now, the present invention will be described in detail.

The product prepared by the present invention is a complex oxide catalyst containing molybdenum, vanadium and tellurium as essential elements. For the purpose of improving the catalytic activities for producing a nitrile, it usually further contains, as a co-catalyst component, at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium. Preferred as such a co-catalyst component, is niobium, tantalum, tungsten, titanium, antimony or bismuth. Particularly preferred is niobium. Taking into consideration the compositional ratios of the respective elements, a complex oxide represented by the following formula (1) is preferred.

$$Mo_aV_bTe_cX_xO_n \qquad (1)$$

wherein X is at least one element selected from the group consisting of Nb, Ta, W, Ti, Al, Zr, Cr, Mn, Fe, Ru, Co, Rh, Ni, Pd, Pt, Sb, Bi, B, In and Ce, when a=1, b=0.01 to 1.0, c=0.01 to 1.0, and x=0 to 1.0, and n is a number such that the total valency of the metal elements is satisfied.

Further, with respect to the coefficients for the respective elements, it is particularly preferred that when $a=1$, $b=0.1$ to $0.6$, $c=0.05$ to $0.4$, and $x=0.01$ to $0.6$.

As the complex oxide, the one having a certain specific crystal structure is preferred. Specifically, preferred is the one which shows the following five main diffraction peaks at the specific diffraction angles of $2\theta$ as the X-ray diffraction pattern of the complex oxide (as measured by using Cu—K$\alpha$-rays as the X-ray source):

| Diffraction angles of $2\theta$ (°) | Center values of X-ray lattice spacing (Å) | Relative Intensity |
|---|---|---|
| 22.1 ± 0.3 | 4.02 | 100 |
| 28.2 ± 0.3 | 3.16 | 20 to 150 |
| 36.2 ± 0.3 | 2.48 | 5 to 60 |
| 45.2 ± 0.3 | 2.00 | 2 to 40 |
| 50.0 ± 0.3 | 1.82 | 2. to 40 |

The intensities of X-ray diffraction peaks may differ depending upon the measuring conditions for the respective crystals. However, the relative intensities based on the peak intensity at $2\theta=22.1°$ being 100, are usually within the above identified ranges. In general, the peak intensities at $2\theta=22.1°$ and $28.2°$ are higher than other.

Now, the process for preparing the above complex oxide catalyst will be described. Firstly, a solution containing essential elements for the catalyst, is prepared. This solution may be a uniform solution or a slurry in a suspension state. As the solvent for this purpose, water is usually employed. However, an organic solvent such as an alcohol, an ester, an ether or a carboxylic acid may also be used. The method for preparing the solution containing essential elements for the catalyst, is not particularly limited, and it may be such that prescribed amounts of starting materials corresponding to the composition of the desired complex oxide are mixed with a solvent such as a water. So long as the mixture forms a uniform solution or slurry, it is unnecessary to heat it or to conduct stirring for a long period of time.

For example, in a case where a catalyst of a complex oxide comprising molybdenum, vanadium, tellurium and niobium is to be prepared, an aqueous solution of telluric acid, an aqueous solution of ammonium niobium oxalate and an aqueous solution of ammonium paramolybdate are sequentially added to a solution containing ammonium metavanadate in such amounts that the atomic ratios of the respective metal elements will be predetermined proportions, to prepare a solution or slurry containing the catalyst components. Here, there is no particular restriction as to the concentration of the solution or slurry. It is common to prepare the solution or slurry so that the total amount of starting material compounds for the catalyst constitutes from 10 to 60% by weight.

The starting materials for the above complex oxide may not be limited to those mentioned above. For example, a wide range of starting materials may be used, including an oxide such as $MoO_3$, $V_2O_5$, $V_2O_3$, $TeO_2$ or $Nb_2O_5$, a halide or oxyhalide such as $MoCl_5$, $VCl_4$, $VOCl_3$ or $NbCl_5$, an alkoxide such as $Mo(OC_2H_5)_5$, $Nb(OC_2H_5)_5$, $VO(OC_2H_5)_3$ or molybdenum acetyl acetonate, and an organic metal compound.

Then, the above solution or slurry is dried by a spray drying method or a freeze-drying method. This is the most characteristic portion of the present invention.

Here, spray drying means a drying method which contains a step of spraying the solution or slurry to form fine liquid droplets, and it can be carried out by means of a commercially available spray drier. The conditions for spray drying may be suitably set depending upon the specification of the spray dryer, the amount of the object to be treated, etc. However, the temperature at the central portion of the spray drier is usually set at a level of from 80° to 400° C., preferably from 120° to 280° C., and a drying gas such as heated air, nitrogen or argon is circulated. The drying gas should have a heat quantity sufficient to evaporate the water content, etc. in the solution or slurry. If the temperature of the drying gas is low, a larger amount of the drying gas will be required. Further, the particle size of solid particles obtainable by spray drying may be adjusted by controlling the rotational speed of the disc and the amount of the supplied solution or slurry. Usually, the average particle size is adjusted, for example, to a level of not more than 100 μm, preferably from 20 to 80 μm.

The freeze-drying method is a method which comprises freezing the solution or slurry, followed by removal of the solvent by sublimation, and such a method can be carried out by using a commercially available freeze-drying machine. It is common to employ a method wherein a uniform solution or slurry containing the starting materials for the catalyst, is cooled and frozen by e.g. liquid nitrogen, followed by drying by means of a freeze-drying machine. The drying conditions may be set in accordance with the specification of the particular freeze-drying machine, and it is common to conduct the freeze-drying under a reduced pressure of from 0.01 to 10 mmHg. There is no particular restriction as to the particle size distribution of the dried product. Even if water remains in a few percent in the dried product which has reached to a constant weight by freeze-drying, such a water content will not adversely affect the performance of the catalyst.

Further, in the present invention, the spray drying method and the freeze-drying method may be used in combination to conduct spray and freeze-drying.

The reason for the improvement in the performance of the catalyst by the above-mentioned specific drying method, is not clearly understood. However, it is conceivable that by the employment of the spray drying method or the freeze-drying method, the physical properties such as the crystal structure, the crystal grain size, the pore volume, the specific surface area, the composition of the outer surface of the catalyst, etc., become suitable for formation of a nitrile. For example, a precursor for the complex oxide comprising metal components of molybdenum, vanadium and tellurium as the main components, may be formed already in the solution or slurry. Then, when the volatile component such as water is instantaneously removed from such a solution or slurry, the precursor already formed in the solution or slurry will remain as a dried product while maintaining its basic structure. It is conceivable that when subjected to heat treatment, such a mixture will be converted to a complex oxide catalyst having a specific crystal structure.

Both methods are characterized in that the volatile component such as water is instantaneously removed. Such a characteristic is believed to be somehow related to the improvement of the catalytic performance. Accordingly, so long as a drying method is based on a principle such that a volatile component such as water is instantaneously removed, such a method is expected to provide effects equal to those obtainable by the spray drying method or the freeze-drying method.

The dried product obtained by the above method is then subjected to heat treatment. For the heat treatment, an optional method may be employed depending upon the nature of the dried product and the scale. However, it is common to employ heat treatment on an evaporating dish or heat treatment by means of a heating furnace such as a rotary furnace or a fluidized calcination furnace. Otherwise, these heat treating methods may be used in a proper combination. With respect to the heat treating conditions, the dried product is heat-treated and calcined usually at a temperature of from 350° to 700° C., preferably from 400° to 650° C. usually for from 0.5 to 30 hours, preferably from 1 to 10 hours. It is also possible to adopt a method in which the heat treating temperature is gradually raised. Specifically, it is possible to employ a method wherein prior to calcination at a temperature of from 350° to 700° C., the dried product is subjected to heat treatment usually at a temperature of from 150° to 350° C. for from 0.5 to 5 hours, and then the temperature is raised for calcination.

With respect to the above heat treating method, it is common to carry out the method in an oxygen atmosphere. However, in order to obtain a catalyst having the above-mentioned specific structure, the atmosphere for calcination is rather desired to be substantially free from oxygen. Specifically, it is preferred to conduct the treatment in an inert gas atmosphere of e.g. nitrogen, argon or helium or in vacuum.

A complex oxide thus obtained has catalytic activities superior to conventional catalysts for producing a nitrile, by itself. However, the catalytic activities can be further improved by pulverizing the complex oxide.

The pulverization method is not particularly limited, and any conventional method may be employed. As a dry system pulverization method, a method of using a gas stream pulverizer may, for example, be mentioned wherein coarse particles are pulverized by collision of the particles to one another under a high speed gas stream. Further, pulverization may be conducted mechanically. In a small scale pulverization, it is possible to employ a pulverization method by means of a mortar or the like.

As a wet system pulverization method wherein water or an organic solvent is added to the complex oxide and pulverization is conducted in a wet state, a method may be employed wherein a conventional rotary cylinder-type medium pulverizer or a medium-stirring type pulverizer is used. The rotary cylinder-type medium pulverizer is a wet system pulverizer of the type wherein a cylindrical container containing a pulverizing medium is rotated, such as a ball mill or a load mill. The medium-stirring type pulverizer is a wet system pulverizer of the type wherein a pulverizing medium contained in a container is stirred by a stirrer, which includes, for example, a screw rotary type and a disk rotary type.

The pulverization conditions may be appropriately set depending upon the nature of the complex oxide and, particularly in the case of a wet type pulverization, depending upon the viscosity, concentration, etc. of the solution as well as the optimum conditions of the pulverizer itself. It is preferred to conduct pulverization until the pulverized complex oxide will have an average particle size of usually at most 20 $\mu$m, preferably at most 5 $\mu$m. By conducting the pulverization to such an extent, a remarkable improvement is observed in the catalytic performance.

The reason for the improvement of the catalytic performance by such pulverization is not clearly understood. However, it appears that with the catalyst of the present invention, the improvement is attributable to the change in the configuration of the catalyst surface rather than to the mere increase of the surface area by pulverization. From electron microscopic inspection of the surface of the complex oxide before and after the pulverization, crystal segments which are scarcely observed before the pulverization, are abundantly observed on the surface of the complex oxide after the pulverization. Accordingly, such crystal segments are believed to act effectively for the reaction.

In some cases, it is also possible to further increase the catalytic activities by adding a solvent to the pulverized catalyst to form a solution or a slurry and drying it again. There is no particular restriction as to the concentration of the solution or slurry. The solution or slurry is adjusted so that the total amount of starting material compounds of the pulverized catalyst precursor is usually from 10 to 60% by weight. Then, this solution or slurry is dried by e.g. a spray drying method, a freeze-drying method, an evaporation and drying method or a vacuum drying method, preferably a spray drying method. Also in the case of a wet system pulverization, similar drying may be carried out.

The catalyst obtained by the above drying or drying followed by pulverization, may be used by itself as a final catalyst. Otherwise, it may be subjected further to heat treatment usually at a temperature of from 200° to 700° C. for from 0.1 to 10 hours.

The obtained complex oxide may be used alone as a solid catalyst, but may be used together with a well known carrier such as silica, alumina, titania, aluminosilicate, diatomaceous earth or zirconia. In such a case, the carrier may be added at any stage during the process for producing the catalyst, and pulverization may be carried out inclusive of the carrier. Further, the carrier may be added after the catalyst has been synthesized. The catalyst produced by the process of the present invention may be molded to have an optional shape and particle size depending upon the scale and the system of the reaction.

A nitrile can be produced by a gas phase catalytic oxidation reaction of an alkane with ammonia in the presence of the catalyst obtained by the process of the present invention.

The alkane as the starting material is not particularly limited and includes, for example, methane, ethane, propane, n-butane, isobutane, pentane, hexane and heptane. It is preferred to employ a $C_{1-4}$ lower alkane, particularly, propane, isobutane or n-butane, in view of the industrial application of the resulting nitrile. The catalyst obtained by the process of the present invention is capable of producing a nitrile by a gas phase catalytic oxidation reaction of an alkene such as propylene or isobutene, with ammonia. A small amount of an alkene may be contained in the above alkane.

The detailed mechanism of the gas phase catalytic oxidation reaction is not clearly understood, but oxidation is conducted by oxygen atoms present in the above catalyst or by molecular oxygen present in a feed gas. When molecular oxygen is present in the feed gas, the molecular oxygen may be pure oxygen gas. However, since no purity is required, it is usually economical to use an oxygen-containing gas such as air. As the feed gas, it is usual to employ a gas mixture comprising an alkane, ammonia and an oxygen-containing gas. However, a gas mixture of an alkane and ammonia, and an oxygen-containing gas may be supplied alternately.

It is also possible to conduct the gas phase catalytic reaction using only an alkane and ammonia as the feed gas, substantially in the absence of molecular oxygen. In such a case, it is advisable that a part of the catalyst is appropriately withdrawn from the reaction zone, the catalyst is then supplied to an oxidation regenerator, and after the regeneration, the catalyst is again supplied to the reaction zone. As a method for regenerating the catalyst, a method may, for example, be mentioned wherein an oxidative gas such as oxygen, air or nitrogen oxide is circulated against the catalyst in the regenerator usually at a temperature of from 300° to 600° C.

A case wherein propane is used as the alkane and air is used as the oxygen source, will be described in further detail. The system of the reactor may be either a fixed bed system or a fluidized bed system. However, since the reaction is exothermic, the fluidized bed system is preferred so that the control of the reaction temperature is thereby easy. The proportion of air to be supplied to the reaction is important for the selectivity for the resulting acrylonitrile. A high selectivity for acrylonitrile is obtainable when air is usually within a range of at most 25 mols, preferably from 1 to 18 mols, per mol of propane. The proportion of ammonia to be supplied to the reaction is usually within a range of from 0.2 to 5 mols, preferably from 0.5 to 3 mols, per mol of propane. This reaction is conducted usually under atmospheric pressure, but it may be carried out under a slightly increased pressure or under a slightly reduced pressure. With respect to other alkanes, the composition of the feed gas may appropriately be selected in accordance with the conditions in the case of propane.

When the catalyst obtained by the process of the present invention is employed, the reaction can be conducted at a temperature lower than the temperature for conventional ammoxidation of alkanes, e.g. at a temperature of from 340° to 480° C., preferably from 400° to 450° C. The gas space velocity SV in the gas phase reaction is usually within a range of from 100 to 10,000 hr$^{-1}$, preferably from 300 to 2,000 hr$^{-1}$. As a diluent gas for adjusting the space velocity and the oxygen partial pressure, an inert gas such as nitrogen, argon or helium, can be employed. When ammoxidation of propane is conducted by means of the catalyst prepared by the process of the present invention, carbon monoxide, carbon dioxide, acetonitrile, hydrocyanic acid, etc. will be produced as by-products in addition to acrylonitrile, but their amounts are very small.

Now, the present invention will be described in further detail with reference to Examples. However, it should be understood that the present invention is by no means restricted to such specific Examples.

In the following Example, the conversion (%), the selectivity (%) and the yield (%) are shown by the following formulas, respectively:

$$\text{Conversion of alkane (\%)} = \frac{\text{mols of consumed alkane}}{\text{mols of supplied alkane}} \times 100$$

$$\text{Selectivity of objective nitrile (\%)} = \frac{\text{mols of objective nitrile obtained}}{\text{mols of consumed alkane}} \times 100$$

$$\text{Yield of objective nitrile (\%)} = \frac{\text{mols of objective nitrile obtained}}{\text{mols of supplied alkane}} \times 100$$

EXAMPLE 1

A catalyst having an empirical formula $Mo_1V_{0.3}Te_{0.23}Nb_{0.1}O_n/SiO_2$ (10 wt %) was prepared as follows.

In 810 ml of warm water, 171.2 g of ammonium paramolybdate, 39.7 g of ammonium metavanadate and 51.2 g of telluric acid were dissolved to obtain a uniform aqueous solution. Further, 123.6 g of silica sol having a silica content of 20 wt % and 139.9 ml of an aqueous solution of ammonium niobium oxalate having a niobium concentration of 0.5 mol/l were mixed thereto to obtain a slurry. This slurry was supplied to a spray dryer at a rate of about 120 ml/min, and dried by removing water while supplying heated air. At that time, the temperature at the central portion of the spray dryer was about 160° C.

The dried product was heat-treated at a temperature of about 300° C. until an ammonia odor disappeared and then calcined in a nitrogen stream at 600° C. for 2 hours.

The powder X-ray diffraction of the catalyst thus obtained, was measured (using Cu-K$\alpha$-rays), whereby main diffraction peaks were observed at diffraction angles of $2\theta$ (°) of 22.2 (100), 28.3 (68.1), 36.3 (17.0), 45.2 (12.6) and 50.1 (10.2) (the numerical values in the brackets indicate the relative peak intensities based on the peak at 22.2° being 100).

0.5 ml of the catalyst thus obtained was packed into a reactor, and the gas phase catalytic oxidation reaction was conducted at a reaction temperature of 420° C. and at a space velocity SV of 1000 hr$^{-1}$ by supplying a feed gas in a molar ratio of propane:ammonia:air = 1:1.2:15. The results are shown in Table 1.

EXAMPLE 2

A catalyst having an empirical formula $Mo_1V_{0.4}Te_{0.2}Nb_{0.1}O_n$ was prepared as follows.

In 1170 ml of warm water, 158.9 g of ammonium paramolybdate, 42.1 g of ammonium metavanadate and 41.3 g of telluric acid were dissolved to obtain a uniform aqueous solution. Further, 180 ml of an aqueous solution of ammonium niobium oxalate having a niobium concentration of 0.5 mol/l was mixed thereto to obtain a slurry. This slurry was supplied to a spray dryer at a rate of about 12 ml/min and dried by removing water while supplying heated air. At that time, the temperature at the central portion of the spray dryer was about 160° C.

Thereafter, heat treatment and calcination in a nitrogen stream were conducted in the same manner as in Example 1. The powder X-ray diffraction of the catalyst thus obtained was measured (using Cu-K$\alpha$-rays), whereby main diffraction peaks were observed at diffraction angles of $2\theta$ (°) of 22.1 (100), 28.2 (92.5), 36.2 (23.0), 45.2 (12.5) and 50.0 (14.0) (the numerical values in the brackets indicate the relative peak intensities based on the peak at 22.1° being 100).

Using the catalyst thus obtained, the gas phase catalytic oxidation reaction of propane was conducted in the same manner as in Example 1. The results are shown in Table 1.

COMPARATIVE EXAMPLE 1

A slurry was prepared in the same manner as in Example 2, and about 100 ml of the slurry was heated on an evaporation dish heated by an electrical heater and boiled with stirring to remove water. It took about 5 minutes for the removal of water.

Thereafter, heat treatment and calcination in a nitrogen stream were conducted in the same manner as in Example 1.

The powder X-ray diffraction of the catalyst thus obtained was measured, whereby in addition to the peaks at diffraction angles of $2\theta$ (°) of 22.1 and 28.2, diffraction peaks appeared at 27 4°, 23 3° and 12 8°, and such peaks were found to be attributable to rhombic molybdenum trioxide from the data base of the powder X-ray diffraction.

Using the catalyst thus obtained, the gas phase catalytic oxidation reaction of propane was conducted in the same manner as in Example 1. The results are shown in Table 1.

EXAMPLE 3

The preparation was conducted in the same manner as in Example 1 except that in Example 1, the amount of ammonium metavanadate was changed to 28.4 g, and the amount of the silica sol having a silica content of 20 wt % was changed to 118.7 g, to obtain a catalyst having an empirical formula $Mo_1V_{0.25}Te_{0.23}Nb_{0.1}O_n/SiO_2$ (10 wt %).

Using this catalyst, the gas phase catalytic oxidation reaction of propane was conducted in the same manner as in Example 1 except that the reaction temperature was changed to 410° C. The results are shown in Table 1.

EXAMPLE 4

The preparation was conducted in the same manner as in Example 1 except that in Example 1, the amount of ammonium metavanadate was changed to 28.4 g, the amount of the silica sol having a silica content of 20 wt % was changed to 122.3 g, and the amount of ammonium niobium oxalate having a niobium concentration of 0.5 mol/l was changed to 290.9 ml, to obtain a catalyst having empirical formula $Mo_1V_{0.25}Te_{0.23}Nb_{0.15}O_n/SiO_2$ (10 wt %).

Using this catalyst, the gas phase catalytic oxidation reaction of propane was conducted in the same manner as in Example 1 except that the reaction temperature was changed to 400° C. The results are shown in Table 1.

EXAMPLE 5

The preparation was conducted in the same manner as in Example 1 except that in Example 1, the amount of ammonium metavanadate was changed to 34.0 g, the amount of the silica sol having a silica content of 20 wt % was changed to 122.6 g, and the amount of ammonium niobium oxalate having a niobium concentration of 0.5 mol/l was changed to 232.7 ml, to obtain a catalyst having an empirical formula $Mo_1V_{0.3}Te_{0.23}Nb_{0.12}O_n/SiO_2$ (10 wt %).

Using this catalyst, the gas phase catalytic oxidation reaction of propane was conducted in the same manner as in Example 1 except that the reaction temperature was changed to 410° C. The results are shown in Table 1.

EXAMPLE 6

The preparation was conducted in the same manner as in Example 1 except that in Example 1, the amount of the silica sol having a silica content of 20 wt % was changed to 127.2 g, and the amount of ammonium niobium oxalate having a niobium concentration of 0.5 mol/l was changed to 290.9 ml, to obtain a catalyst having an empirical formula $Mo_1V_{0.3}Te_{0.23}Nb_{0.15}O_n/SiO_2$ (10 wt %).

Using this catalyst, the gas phase catalytic oxidation reaction of propane was conducted in the same manner as in Example 1. The results are shown in Table 1.

EXAMPLE 7

The preparation was conducted in the same manner as in Example 1 except that in Example 1, the amount of ammonium metavanadate was changed to 45.4 g, the amount of the silica sol having a silica content of 20 wt % was changed to 129.6 g, and the amount of ammonium niobium oxalate having a niobium concentration of 0.5 mol/l was changed to 290.9 ml, to obtain a catalyst having an empirical formula $Mo_1V_{0.4}Te_{0.23}Nb_{0.15}O_n/SiO_2$ (10 wt %).

Using this catalyst, the gas phase catalytic oxidation reaction of propane was conducted in the same manner as in Example 1. The results are shown in Table 1.

EXAMPLE 8

The preparation was conducted in the same manner as in Example 1 except that in Example 1, the amount of telluric acid was changed to 66.8 g, the amount of the silica sol having a silica content of 20 wt % was changed to 129.2 g, and the amount of ammonium niobium oxalate having a niobium concentration of 0.5 mol/l was changed to 232.7 ml, to obtain a catalyst having an empirical formula $Mo_1V_{0.3}Te_{0.3}Nb_{0.12}O_n/SiO_2$ (10 wt %).

Using this catalyst, the gas phase catalytic oxidation reaction of propane was conducted in the same manner as in Example 1 except that the reaction temperature was changed to 410° C. The results are shown in Table 1.

EXAMPLE 9

The preparation was conducted in the same manner as in Example 1 except that in Example 1, the amount of ammonium metavanadate was changed to 34.0 g, the amount of telluric acid was changed to 44.5 g, the amount of the silica sol having a silica content of 20 wt % was changed to 119.7 g, and the amount of ammonium niobium oxalate having a niobium concentration of 0.5 mol/l was changed to 232.7 ml, to obtain a catalyst having an empirical formula $Mo_1V_{0.3}Te_{0.2}Nb_{0.12}O_n/SiO_2$ (10 wt %).

Using this catalyst, the gas phase catalytic oxidation reaction of propane was conducted in the same manner as in Example 1 except that the reaction temperature was changed to 410° C. The results are shown in Table 1.

EXAMPLE 10

The preparation was conducted in the same manner as in Example 1 except that in Example 1, the amount of ammonium metavanadate was changed to 34.0 g, the amount of telluric acid was changed to 35.6 g, the amount of the silica sol having a silica content of 20 wt % was changed to 119.7 g, and the amount of ammonium niobium oxalate having a niobium concentration of 0.5 mol/l was changed to 232.7 ml, to obtain a catalyst having an empirical formula $Mo_1V_{0.3}Te_{0.16}Nb_{0.12}O_n/SiO_2$ (10 wt %).

Using this catalyst, the gas phase catalytic oxidation reaction of propane was conducted in the same manner as in Example 1 except that the reaction temperature was changed to 410° C. The results are shown in Table 1.

EXAMPLE 11

The preparation was conducted in the same manner as in Example 1 except that in Example 1, the amount of ammonium metavanadate was changed to 34.0 g, the amount of telluric acid was changed to 28.9 g, the amount of the silica sol having a silica content of 20 wt % was changed to 113.1 g, and the amount of ammonium niobium oxalate having a niobium concentration of 0.5 mol/l was changed to 232.7 ml, to obtain a catalyst having an empirical formula $Mo_1V_{0.3}Te_{0.13}Nb_{0.12}O_n/SiO_2$ (10 wt %).

Using this catalyst, the gas phase catalytic oxidation reaction of propane was conducted in the same manner as in Example 1 except that the reaction temperature was changed to 430° C. The results are shown in Table 1.

EXAMPLE 12

A catalyst having an empirical formula $Mo_1V_{0.3}Te_{0.23}Nb_{0.12}O_n$ was prepared as follows.

In 47 ml of warm water, 7.06 g of ammonium paramolybdate $(NH_4)_6Mo_7O_{24}\cdot 4H_2O$ was dissolved, and 1.41 g of ammonium metavanadate $NH_4VO_3$ and 2.11 g of telluric acid $H_6TeO_6$ were sequentially added thereto, to obtain a uniform aqueous solution. To this solution, 12.13 g of an aqueous solution of ammonium niobium oxalate having a niobium concentration of 0.396 mol/kg was mixed. This solution was dropwise added to a flask made of glass cooled by liquid nitrogen and freezed. Then, water was removed therefrom by a freeze-drying method to obtain a dried product. This dried product was calcined in a nitrogen stream at 600° C. for 2 hours.

The powder X-ray diffraction of the catalyst thus obtained, was measured (using Cu-Kα-rays), whereby main diffraction peaks at diffraction angles of 2θ (°) of 22.1 (100), 28.2 (78.3), 36.2 (20.2), 45.1 (15.1) and 50.0 (12.4) were observed (the numeral values in the brackets represent relative peak intensities based on the peak at 22.1° being 100).

0.35 g of the catalyst thus obtained was packed into a reactor, and the gas phase catalytic oxidation reaction was conducted at a reaction temperature of 410° C. at a space velocity SV of about 1500 hr$^{-1}$ by supplying a feed gas in a molar ratio of propane:ammonia:air =1:1.2:15. The results are shown in Table 2.

EXAMPLE 13

A catalyst having an empirical formula $Mo_1V_{0.3}Te_{0.2}Nb_{0.14}O_n$ was prepared as follows.

In 65 ml of warm water, 7.06 g of ammonium paramolybdate $(NH_4)_6Mo_7O_{24}\cdot 4H_2O$ was dissolved, and 1.41 g of ammonium metavanadate $NH_4VO_3$ and 1.84 g of telluric acid $H_6TeO_6$ were sequentially added to obtain a uniform aqueous solution. To this solution, 14.46 g of an aqueous solution of ammonium niobium oxalate having a niobium concentration of 0.387 mol/kg was mixed. This solution was sprayed to the inner wall of a glass flask cooled by liquid nitrogen and freezed. Water was removed therefrom by a freeze-drying method to obtain a dried product. This dried product was calcined in a nitrogen stream at 600° C. for 2 hours.

0.55 g of the catalyst thus obtained was packed into a reactor, and the gas phase catalytic oxidation reaction was conducted at a reaction temperature of 410° C. at a space velocity SV of about 920 hr$^{-1}$ by supplying a feed gas in a molar ratio of propane:ammonia:air=1:1.2:15. The results are shown in Table 2.

TABLE 1

| | Composition of catalyst | Conversion of propane (%) | Selectivity for acrylonitrile (%) | Yield of acrylonitrile (%) |
| --- | --- | --- | --- | --- |
| Example 1 | $Mo_1V_{0.35}Te_{0.23}Nb_{0.1}O_n/SiO_2$(10 wt %) | 88.4 | 60.1 | 53.1 |
| Example 2 | $Mo_1V_{0.4}Te_{0.2}Nb_{0.1}O_n$ | 78.5 | 60.5 | 47.5 |
| Comparative Example 1 | $Mo_1V_{0.4}Te_{0.2}Nb_{0.1}O_n$ | 45.9 | 34.4 | 15.8 |
| Example 3 | $Mo_1V_{0.25}Te_{0.23}Nb_{0.1}O_n/SiO_2$(10 wt %) | 74.4 | 57.3 | 42.6 |
| Example 4 | $Mo_1V_{0.25}Te_{0.23}Nb_{0.15}O_n/SiO_2$(10 wt %) | 66.0 | 63.2 | 41.7 |
| Example 5 | $Mo_1V_{0.3}Te_{0.23}Nb_{0.12}O_n/SiO_2$(10 wt %) | 84.4 | 62.1 | 52.7 |
| Example 6 | $Mo_1V_{0.35}Te_{0.23}Nb_{0.15}O_n/SiO_2$(10 wt %) | 85.2 | 61.5 | 52.4 |
| Example 7 | $Mo_1V_{0.4}Te_{0.23}Nb_{0.15}O_n/SiO_2$(10 wt %) | 69.8 | 59.6 | 41.6 |
| Example 8 | $Mo_1V_{0.3}Te_{0.3}Nb_{0.12}O_n/SiO_2$(10 wt %) | 65.8 | 61.9 | 40.7 |
| Example 9 | $Mo_1V_{0.3}Te_{0.2}Nb_{0.12}O_n/SiO_2$(10 wt %) | 83.3 | 63.5 | 52.9 |
| Example 10 | $Mo_1V_{0.3}Te_{0.16}Nb_{0.12}O_n/SiO_2$(10 wt %) | 83.4 | 63.6 | 53.1 |
| Example 11 | $Mo_1V_{0.3}Te_{0.13}Nb_{0.12}O_n/SiO_2$(10 wt %) | 64.3 | 58.4 | 37.5 |

TABLE 2

| | Composition of catalyst | Conversion of propane (%) | Selectivity for acrylonitrile (%) | Yield of acrylonitrile (%) |
| --- | --- | --- | --- | --- |
| Example 12 | $Mo_1V_{0.3}Te_{0.23}Nb_{0.12}O_n$ | 84.0 | 63.7 | 53.5 |
| Example 13 | $Mo_1V_{0.3}Te_{0.2}Nb_{0.14}O_n$ | 92.1 | 59.1 | 54.4 |

EXAMPLE 14

A catalyst having an empirical formula $Mo_1V_{0.35}Te_{0.23}Nb_{0.12}O_n$ was prepared as follows.

In 3250 ml of warm water, 789 g of ammonium paramolybdate, 157 g of ammonium metavanadate and 236 g of telluric acid were dissolved to obtain a uniform aqueous solution. Further, 1175 ml of an aqueous solution of ammonium niobium oxalate having a niobium concentration of 0.456 mol/kg was mixed thereto to obtain a slurry. This slurry was heated and spray-dried. This dried product was heat-treated in a nitrogen stream at 600° C. for 2 hours. 5 g of the catalyst precursor thus obtained was pulverized in an agate mortar until the average particle size became at most 20 μm and then heat-treated in a nitrogen stream at 600° C. for 2 hours.

0.5 ml of the catalyst thus obtained was packed into a reactor, and the gas phase catalytic oxidation reaction was conducted at a reaction temperature of 410° C. and at a space velocity SV of 1000 hr$^{-1}$ by supplying a feed gas in a molar ratio of propane:ammonia:air=1:1.2:15. The results are shown in Table 3.

Further, a scanning electron microscopic photograph of the surface of the above catalyst is shown in FIG. 1. It is evident from FIG. 1 that many crystal segments are present on the catalyst surface.

EXAMPLE 15

2 kg of water was added to 500 g of a catalyst precursor obtained in the same manner as in Example 14 to obtain a slurry. The slurry was pulverized in a ball mill for one hour. By this pulverization, the average particle size of the catalyst precursor was changed from 50 μm to 0.5 μm. The slurry containing the catalyst precursor thus pulverized, was spray-dried and then heat-treated in a nitrogen stream at 600° C. for 2 hours. Using the catalyst thus obtained, the gas phase catalytic oxidation reaction of propane was conducted under the same reaction conditions as in Example 1. The results are shown in Table 3.

EXAMPLE 16

Using the catalyst of Example 15, the gas phase catalytic oxidation reaction of propane was conducted in the same manner as in Example 15 except that the space velocity SV was changed to 1500 hr$^{-1}$. The results are shown in Table 3.

EXAMPLE 17

Using the catalyst of Example 15, the gas phase catalytic oxidation reaction of propane was conducted in the same manner as in Example 16 except that the reaction temperature was changed to 420° C. The results are shown in Table 3.

EXAMPLE 18

Figure 2:
FIG. 2 is a photograph showing the surface of the catalyst particles obtained in Example 18 (10,000 magnifications).

Using the catalyst precursor of Example 14 as the catalyst by itself without pulverization, the gas phase catalytic oxidation reaction of propane was conducted in the same manner as in Example 14. The results are shown in Table 3. Further, a scanning electron microscopic photograph of the surface of the catalyst is shown in FIG. 2. From comparison of Example 14 and Example 18, it is evident that there is a difference in the state of the catalyst surface depending upon whether or not pulverization was conducted (see FIGS. 1 and 2). Further, it is evident that the yield of acrylonitrile is higher in Example 14 wherein the pulverized catalyst was employed, than in Example 18 (see Table 3).

TABLE 3

| Example | Space velocity SV (hr$^{-1}$) | Reaction temp. (°C.) | Conversion of propane (%) | Selectivity for acrylonitrile (%) | Yield of acrylonitrile (%) |
| --- | --- | --- | --- | --- | --- |
| 14 | 1000 | 410 | 95.1 | 58.4 | 55.5 |
| 15 | 1000 | 410 | 95.0 | 59.7 | 56.7 |
| 16 | 1500 | 410 | 84.2 | 66.2 | 55.7 |
| 17 | 1500 | 420 | 89.4 | 64.3 | 57.5 |
| 18 | 1000 | 460 | 86.8 | 59.2 | 52.0 |

EXAMPLE 19

A catalyst having an empirical formula $Mo_1V_{0.30}Te_{0.23}O_n$ was prepared in the same manner as in Example 1 except that the silica sol and ammonium niobium oxalate were not used.

0.5 ml of the catalyst thus obtained was packed into a reactor, and the gas phase catalytic oxidation reaction was conducted at a reaction temperature of 440° C. and a space velocity SV of 1000 hr$^{-1}$ by supplying a feed gas in a molar ratio of propane:ammonia:air=1:1.2:15. The results are shown in Table 4.

COMPARATIVE EXAMPLE 2

A catalyst having an empirical formula $Mo_1V_{0.30}Te_{0.23}O_n$ was prepared in the same manner as in Example 19 except that amount 100 ml of the slurry was heated on an evaporation dish heated by an electrical heater and boiled with stirring to remove water, instead of spray drying the slurry.

Using the catalyst thus obtained, the gas phase catalytic oxidation reaction was conducted under the same conditions as in Example 19 except that the reaction temperature was changed to 460° C. The results are shown in Table 4.

TABLE 4

|  | Reaction temp. (°C.) | Conversion of propane | Selectivity for acrylonitrile (%) | Yield of acrylonitrile (%) |
| --- | --- | --- | --- | --- |
| Example 19 | 440 | 35.4 | 16.9 | 5.4 |
| Comparative Example 2 | 460 | 7.5 | 2.0 | 1.5 |

EXAMPLES 20 to 22

A Mo—V—Te—O catalyst was prepared in the same manner as in Example 19 by properly adjusting the amounts of the starting compounds in Example 19.

0.5 ml of the catalyst thus obtained was packed into a reactor, and the gas phase catalytic oxidation reaction was conducted under the reaction conditions as identified in Table 5 by supplying a feed gas in a molar ratio of propane:ammonia:air=1:1.2:10. The results are shown in Table 5.

TABLE 5

| Example | Composition of catalyst | Space velocity SV (hr$^{-1}$) | Reaction temp. (°C.) | Conversion of propane (%) | Selectivity for acrylonitrile (%) | Yield of acrylonitrile (%) |
| --- | --- | --- | --- | --- | --- | --- |
| 20 | $Mo_1V_{0.2}Te_{0.1}O_n$ | 1000 | 440 | 60.1 | 50.7 | 30.5 |

TABLE 5-continued

| Example | Composition of catalyst | Space velocity SV ($hr^{-1}$) | Reaction temp. (°C.) | Conversion of propane (%) | Selectivity for acrylonitrile (%) | Yield of acrylonitrile (%) |
|---|---|---|---|---|---|---|
| 21 | $Mo_1V_{0.52}Te_{0.08}O_n$ | 1000 | 450 | 52.1 | 41.1 | 21.6 |
| 22 | $Mo_1V_{0.12}Te_{0.06}O_n$ | 500 | 440 | 47.7 | 40.4 | 19.3 |

COMPARATIVE EXAMPLES 3 TO 5

A catalyst having an empirical formula $Mo_1Te_{0.5}Al_{12.8}O_n$ was prepared as follows.

Using aluminum nitrate as the aluminum starting material and properly adjusting the amounts of other starting material compounds, a slurry of about 20 wt % was prepared. This slurry was heated on an evaporation dish heated by an electric heater to remove water. The dried product was calcined in an air stream at 600° C. for 3 hours.

1.5 ml of the catalyst thus obtained was packed into a reactor, and the gas phase catalytic oxidation reaction was conducted under the reaction conditions as identified in Table 6 by supplying a feed gas in a molar ratio of propane:ammonia:air=1:1.2:15. The results are shown in Table 6.

COMPARATIVE EXAMPLES 6 to 8

A catalyst was prepared in the same manner as in Comparative Examples 3 to 5 except that the slurry was dried by spray drying instead of the evaporation method.

1.5 ml of the catalyst thus obtained was packed into a reactor, and the gas phase catalytic oxidation reaction was conducted under the reaction conditions as identified in Table 6 by supplying a feed gas in a molar ratio of propane:ammonia:air=1:1.2:15. The results are shown in Table 6.

From Table 6, it is evident that with a Mo—Te—Al—O type complex compound, no improvement in the catalytic activity was observed by spray drying.

4. The process according to claim 1, wherein the heat-treated product is further pulverized.

5. The process according to claim 4, wherein the pulverization is dry-system pulverization.

6. The process according to claim 4, wherein the pulverization is wet-system pulverization.

7. The process according to claim 4, wherein the average particle size of the pulverized catalyst is at most 20 μm.

8. The process according to claim 4, wherein a solvent is added to the pulverized product, and the resulting solution or slurry is dried.

9. The process according to claim 4, wherein the pulverized product is heat-treated.

10. The process according to claim 1, wherein the solution or slurry containing molybdenum, vanadium and tellurium, further contains at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium.

11. The process according to claim 1, wherein the solution or slurry containing molybdenum, vanadium and tellurium, further contains niobium.

12. The process according to claim 1, wherein the solution or slurry containing molybdenum, vanadium and tellurium, further contains silica.

13. The process according to claim 1, wherein the catalyst is represented by the following formula (1):

$$Mo_aV_bTe_cX_xO_n \qquad (1)$$

TABLE 6

| Comparative Example | Space velocity SV ($hr^{-1}$) | Reaction temp. (°C.) | Conversion of propane (%) | Selectivity for acrylonitrile (%) | Yield of acrylonitrile (%) |
|---|---|---|---|---|---|
| 3 | 167 | 420 | 9.4 | 37.8 | 3.5 |
| 4 | 167 | 480 | 28.3 | 61.7 | 17.5 |
| 5 | 167 | 500 | 34.6 | 56.7 | 19.6 |
| 6 | 265 | 440 | 6.6 | 51.8 | 3.4 |
| 7 | 265 | 460 | 9.6 | 56.0 | 5.4 |
| 8 | 265 | 510 | 21.9 | 39.8 | 8.7 |

With the catalyst produced by the process of the present invention, the desired nitrile can be produced in good yield using an alkane as the starting material at a relatively low temperature at a level of from 400° to 450° C. without the necessity of the presence of a halide or water in the reaction system.

We claim:

1. A process for preparing a catalyst useful for producing a nitrile by a gas phase catalytic oxidation reaction of an alkane with ammonia, which comprises drying a solution or slurry containing molybdenum, vanadium and tellurium by a spray drying method or a freeze-drying method and heat-treating the resulting dried product.

2. The process according to claim 1, wherein the heat-treatment is carried out in the absence of oxygen.

3. The process according to claim 1, wherein the heat-treatment is carried out at a temperature of from 350° to 700° C.

wherein X is at least one element selected from the group consisting of Nb, Ta, W, Ti, Al, Zr, Cr, Mn, Fe, Ru, Co, Rh, Ni, Pd, Pt, Sb, Bi, B, In and Ce, when a=1, b=0.01 to 1.0, c=0.01 to 1.0, and x=0 to 1.0, and n is a number such that the total valency of the metal elements is satisfied.

14. The process according to claim 13, wherein in the formula (1), x=0.01 to 0.6.

15. The process according to claim 1, wherein the catalyst has X-ray diffraction peaks at the following diffraction angles of 2θ in its X-ray diffraction pattern:

Diffraction angles of 2θ (°)
22.1±0.3
28.2±0.3
36.2±0.3
45.2±0.3
50.0±0.3

16. A catalyst useful for producing a nitrile by a gas phase catalytic oxidation reaction of an alkane with ammonia, prepared by the process steps comprising:
i) drying a solution or slurry containing molybdenum, vanadium and tellurium by a spray drying method or a freeze-drying method; and
ii) heat-treating the resulting dried product.

17. The catalyst according to claim 16, wherein heat-treatment is carried out in the absence of oxygen.

18. The catalyst according to claim 16, wherein heat-treatment is carried out at a temperature of from 350° to 700° C.

19. The catalyst according to claim 16, wherein the heat-treated product is further pulverized.

20. The catalyst according to claim 19, wherein said heat-treated product is pulverized by dry-system pulverization.

21. The catalyst according to claim 19, wherein said heat-treated product is pulverized by wet-system pulverization.

22. The catalyst according to claim 19, wherein the average particle size of the pulverized catalyst is at most 20 μm.

23. The catalyst according to claim 19, wherein a solvent is added to the pulverized product, and the resulting solution or slurry is dried.

24. The catalyst according to claim 19, wherein the pulverized product is heat-treated.

25. The catalyst according to claim 16, wherein said solution or slurry containing molybdenum, vanadium and tellurium, further contains at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium.

26. The catalyst according to claim 16, wherein said solution or slurry containing molybdenum, vanadium and tellurium, further contains niobium.

27. The catalyst according to claim 16, wherein said solution or slurry containing molybdenum, vanadium and tellurium, further contains silica.

28. The catalyst according to claim 16, wherein said catalyst is represented by the following formula (1):

$$Mo_a V_b Te_c X_x O_n \qquad (1)$$

wherein X is at least one element selected from the group consisting of Nb, Ta, W, Ti, Al, Zr, Cr, Mn, Fe, Ru, Co, Rh, Ni, Pd, Pt, Sb, Bi, B, In and Ce, when a=1, b=0.01 to 1.0, c=0.01 to 1.0, and x=0 to 1.0, and n is a number such that the total valency of the metal elements is satisfied.

29. The catalyst according to claim 28, wherein in the formula (1), x=0.01 to 0.6.

30. The catalyst according to claim 16, wherein the catalyst has X-ray diffraction peaks at the following diffraction angles of 2θ in its X-ray diffraction pattern:

Diffraction angles of 2θ (°)
22.1±0.3
28.2±0.3
36.2±0.3
45.2±0.3
50.0±0.3.

* * * * *